(12) United States Patent
Gilton

(10) Patent No.: US 6,593,759 B2
(45) Date of Patent: *Jul. 15, 2003

(54) APPARATUSES AND METHODS FOR DETERMINING IF PROTECTIVE COATINGS ON SEMICONDUCTOR SUBSTRATE HOLDING DEVICES HAVE BEEN COMPROMISED

(75) Inventor: Terry Gilton, Boise, ID (US)

(73) Assignee: Micron Technology, Inc., Boise, ID (US)

(*) Notice: Subject to any disclaimer, the term of this patent is extended or adjusted under 35 U.S.C. 154(b) by 0 days.

This patent is subject to a terminal disclaimer.

(21) Appl. No.: 10/116,595

(22) Filed: Apr. 2, 2002

(65) Prior Publication Data

US 2002/0118028 A1 Aug. 29, 2002

Related U.S. Application Data

(63) Continuation of application No. 09/375,879, filed on Aug. 17, 1999, now Pat. No. 6,411,110.

(51) Int. Cl.[7] .......................... G01R 27/08; G01R 31/00
(52) U.S. Cl. ........................ 324/718; 324/450; 324/501; 324/54; 324/514; 324/551
(58) Field of Search ........................ 435/6, 4; 324/71.1, 324/71.5, 718, 671, 501, 537, 753, 96, 750, 450, 541, 544, 557, 693; 438/8

(56) References Cited

U.S. PATENT DOCUMENTS

| | | | | |
|---|---|---|---|---|
| 3,855,531 A | | 12/1974 | Fielibert et al. | 324/693 |
| 3,874,959 A | * | 4/1975 | Hoekstra | 156/7 |
| 3,989,388 A | | 11/1976 | Sparr, Sr. | 401/11 |
| 4,180,771 A | * | 12/1979 | Guckel | 324/71 |
| 5,164,319 A | * | 11/1992 | Hafeman et al. | 435/291 |
| 5,338,390 A | * | 8/1994 | Barbee et al. | 156/627 |
| 5,480,511 A | * | 1/1996 | Barbee et al. | 156/627.1 |
| 5,516,399 A | * | 5/1996 | Balconi-Lamica et al. | 156/627.1 |
| 5,559,428 A | * | 9/1996 | Li et al. | 324/71.5 |
| 5,573,624 A | * | 11/1996 | Barbee et al. | 156/345.1 |
| 5,653,939 A | * | 8/1997 | Hollis et al. | 422/50 |
| 5,869,244 A | * | 2/1999 | Martin et al. | 435/6 |
| 5,985,126 A | * | 11/1999 | Bleck et al. | 205/123 |
| 6,020,264 A | * | 2/2000 | Lustig et al. | 438/692 |
| 6,051,422 A | * | 4/2000 | Kovacs et al. | 435/287.1 |
| 6,072,313 A | * | 6/2000 | Li et al. | 324/230 |
| 6,097,205 A | * | 8/2000 | Liberman et al. | 324/765 |
| 6,150,106 A | * | 11/2000 | Martin et al. | 435/6 |

OTHER PUBLICATIONS

Merriam–Webster's Collegiate Dictionary, p. 1257, tenth edition, 1998.*

* cited by examiner

*Primary Examiner*—N. Le
*Assistant Examiner*—Wasseem H Hamdan
(74) *Attorney, Agent, or Firm*—Wells St. John P.S.

(57) ABSTRACT

In one aspect, the invention includes an apparatus having a semiconductor substrate receiving device with at least one extension configured to hold a semiconductor substrate within a liquid bath. The device is configured to have at least a portion of the extension at least periodically placed within the liquid bath. The extension includes a conductive material at least partially coated with an insulative protective material. The insulative protective material is configured to protect the portion of the conductive material which is in the bath from physically contacting the liquid of the bath. The apparatus also includes an electrode within the bath, and an electrical connection between the electrode and the conductive material of the extension. Additionally, the apparatus has a monitor configured to monitor a current flow state of a circuit that includes the electrode, conductive material of the extension, and liquid bath to determine if the circuit is in a closed state or in an open state. In another aspect, the invention includes methods for determining if a protective coating on a semiconductor substrate receiving device has been compromised.

8 Claims, 1 Drawing Sheet

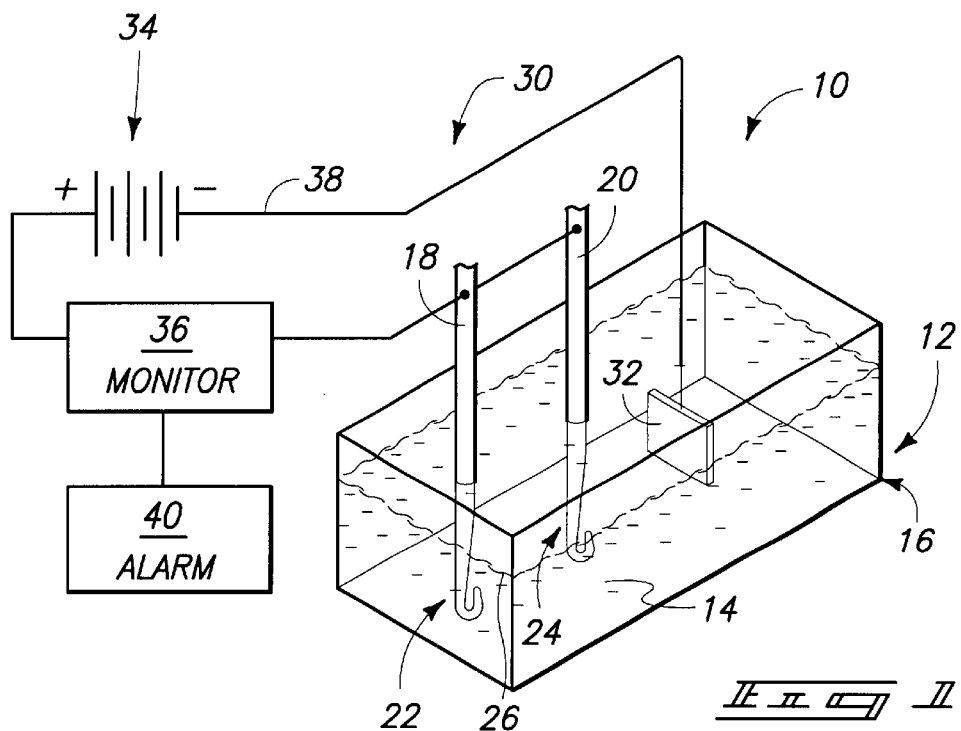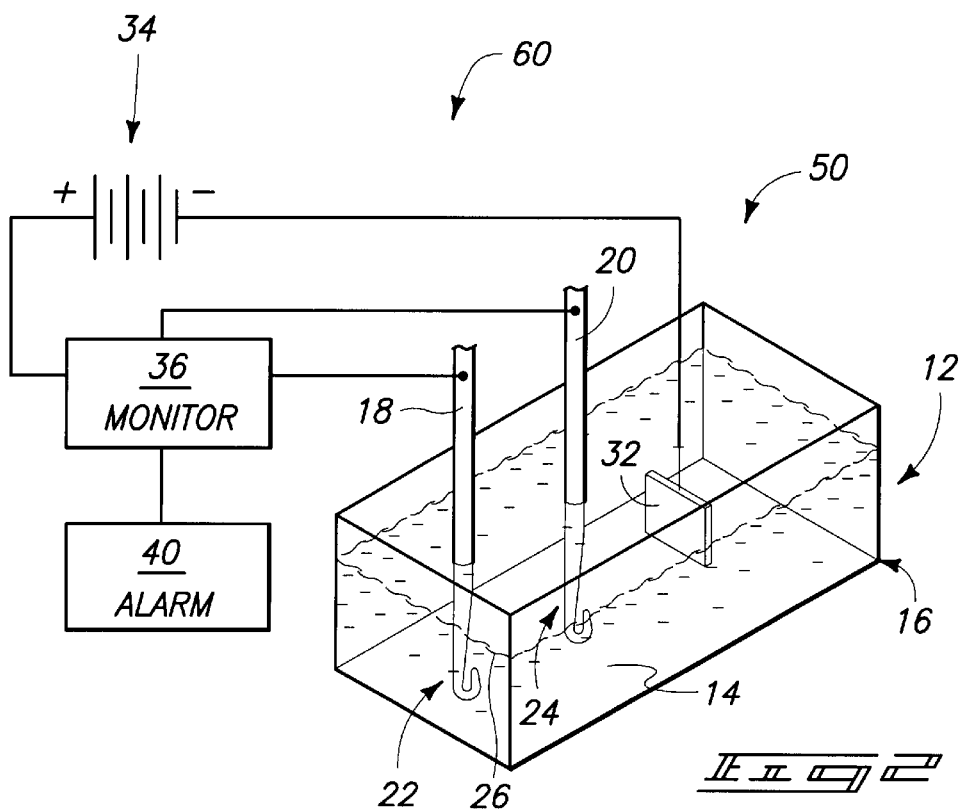

APPARATUSES AND METHODS FOR DETERMINING IF PROTECTIVE COATINGS ON SEMICONDUCTOR SUBSTRATE HOLDING DEVICES HAVE BEEN COMPROMISED

RELATED PATENT DATA

This application is a continuation of U.S. patent application Ser. No. 09/375,879, which was filed on Aug. 17, 1999, now U.S. Pat. No. 6,411,110B1, naming Terry L. Gilton as the inventor and which is incorporated by reference herein.

TECHNICAL FIELD

The invention pertains to methodology and apparatuses associated with treating semiconductor substrates in liquid baths. In particular aspects, the invention pertains to methodology and apparatuses associated with determining if a protective coating on a semiconductor substrate receiving device has been compromised.

BACKGROUND OF THE INVENTION

In modern semiconductor processing, it is frequently desired to insert semiconductive material wafers into liquid baths. Such baths can comprise chemicals which would be corrosive to metal parts. For instance, a bath comprising $H_2SO_4:H_2O_2:H_2O$ (6:1:1, by volume) at about 120° C. is utilized for stripping photoresist as well as for cleaning organic materials from over semiconductive material substrates. As another example, $H_3PO_4$ (85%:15% $H_3PO_4$ to $H_2O$, by volume) at about 160° C. is utilized for etching $Si_3N_4$. In yet another example, dilute hydrofluoric acid (about 49% hydrofluoric acid in water (by weight)) is utilized to etch oxide.

Due to the corrosive nature of baths, like those above, relative to steel, apparatuses configured to retain semiconductive material substrates within a bath typically utilize non-steel materials for those portions of the apparatus that will be dipped within the bath. Such non-steel materials include, for example, quartz and Teflon™. However, the non-steel materials can have structural disadvantages when compared to steel. Accordingly, it can be desirable to utilize steel for portions of a semiconductive substrate treatment apparatus that are dipped into a corrosive bath.

One method of utilizing steel for such portions of a semiconductive substrate treatment apparatus is to coat the steel with a protective coating, such as, for example, Teflon™ (polytetrafluoroethylene or PTFE) or poly(vinylidene fluoride) (PVDF). The coating provides a barrier over steel portions of a semiconductor wafer treatment apparatus that are dipped within a corrosive bath. A problem occurring with such coatings is that semiconductor wafers can comprise sharp edges, and such edges can cut through the protective coatings to expose the steel material thereunder. The exposed steel material can then be corroded by the chemicals in a bath. The corrosion can pollute the bath and eventually destroy the structural integrity of the steel material.

It would be desirable to develop methods for identifying if a protective coating provided over a steel material has been compromised. It would be particularly desirable to develop methods which would identify a compromised protective coating before the structural integrity of an underlying steel material is destroyed by exposure to corrosive baths.

SUMMARY OF THE INVENTION

In one aspect, the invention includes an apparatus configured to measure an electrical conductivity between an insulatively coated conductive semiconductor substrate receiving device and a bath within which the device is submerged. Such measurement can determine if the insulative coating has been compromised.

In another aspect, the invention includes an apparatus comprising a semiconductor substrate receiving device with at least one extension configured to hold a semiconductor substrate within a liquid bath. The device is configured to have at least a portion of the extension at least periodically placed within the liquid bath. The extension comprises a conductive material at least partially coated with an insulative protective material. The insulative protective material is configured to protect the portion of the conductive material which is in the bath from physically contacting the liquid of the bath. The apparatus also comprises an electrode within the bath, and an electrical connection between the electrode and the conductive material of the extension. Additionally, the apparatus comprises a monitor configured to monitor a current flow state of a circuit comprising the electrode, conductive material of the extension, and liquid bath to determine if the circuit is in a closed state (which enables a current flow) or in an open state (which does not enable the current flow).

In yet another aspect, the invention includes methods for determining if a protective coating on a semiconductor substrate receiving device has been compromised.

BRIEF DESCRIPTION OF THE DRAWINGS

Preferred embodiments of the invention are described below with reference to the following accompanying drawings.

FIG. 1 is a diagrammatic view of a semiconductor treatment apparatus of the present invention.

FIG. 2 is a diagrammatic view of another semiconductor treatment apparatus of the present invention.

DETAILED DESCRIPTION OF THE PREFERRED EMBODIMENTS

This disclosure of the invention is submitted in furtherance of the constitutional purposes of the U.S. patent Laws "to promote the progress of science and useful arts"(Article 1, Section 8).

An apparatus 10 encompassed by the present invention is described with reference to FIG. 1. Such apparatus is configured to determine if a protective coating on a semiconductor substrate receiving device has been compromised. The apparatus comprises a bath 12 defined by a fluid 14 contained within a vessel 16. Fluid 14 can, for example, be a liquid corrosive to metallic materials. Such liquid can comprise, for example, the phosphoric acid bath, sulfuric acid/peroxide bath, or hydrofluoric acid bath described above with reference to the prior art.

A pair of semiconductor substrate receiving devices 18 and 20 (which can also be referred to as lifting devices) are shown partially submerged within the fluid 14 of bath 12. The devices 18 and 20 can be referred to as end effectors, and the protective insulative material provided over devices 18 and 20 can be referred to as an end effector coating.

Devices 18 and 20 comprise extensions 22 and 24, respectively, configured to extend within bath 12 and configured to ultimately hold a semiconductor substrate (not shown) within fluid 14. For purposes of interpreting this disclosure and the claims that follow, the terms "semiconductive substrate" and "semiconductor wafer" are defined to mean any construction comprising semiconductive material, including, but not limited to, bulk semiconductive materials such as a semiconductive wafer (either alone or in assemblies comprising other materials thereon), and semiconductive material layers (either alone or in assemblies comprising other materials). The term "substrate" refers to any supporting structure, including, but not limited to, the semiconductive substrates described above. In particular applications of the present invention, a semiconductor substrate will comprise a monocrystalline silicon wafer.

Devices 18 and 20 can be configured to be displaced relative to bath 12 such that devices 18 and 20 can be lifted from, and inserted into, bath 12. Semiconductor substrates can be inserted into bath 12 as devices 18 and 20 are lowered into the bath, and then lifted from bath 12 as devices 18 and 20 are removed from the bath. The cycling of devices 18 and 20 into and out of bath 12 causes a portion of devices 18 and 20 (notably, extensions 22 and 24) to be periodically placed within fluid 14.

Devices 18 and 20 comprise a conductive material (such as, for example, steel) coated with an insulative protective material (such as, for example, PTFE or PTVF). The insulative material protects portions of the conductive material which are inserted into the bath from physically contacting the liquid of the bath. Accordingly, the insulative coating protects conductive portions of devices 18 and 20 from being corroded by the fluid 14 of bath 12.

In the shown embodiment, devices 18 and 20 comprise hooks at extensions 22 and 24 for receiving semiconductor substrates (not shown). It is to be understood, however, that devices 18 and 20 could comprise other configurations for receiving semiconductor substrates, such as, for example, retaining clips, pins, etc. Also, it is to be understood that semiconductor substrates received by devices 18 and 20 can be held within separate containers (not shown), with the containers being received by devices 18 and 20. Accordingly, each of devices 18 and 20 can retain one or more containers of semiconductor substrates and accordingly be utilized to treat a batch of contained substrates. Further, it is noted that devices 18 and 20 can receive semiconductor substrates by providing a tray that extends between devices 18 and 20 and which is configured to retain semiconductor substrates.

Apparatus 10 comprises a circuit 30. Such circuit comprises an electrode 32, a power source 34, and a monitor 36. Electrode 32 is inserted within bath 14 and preferably comprises a material substantially resistant to the corrosive properties of the bath. Such electrode can comprise, for example, carbon, platinum or silicon. Power source 34 can comprise either an alternating current (AC) or direct current (DC) source, and preferably comprises a DC source providing a power of less than or equal to about 24 volts. The low power is preferably utilized to reduce a chance of injury to persons that may inadvertently contact bath 12. Circuit 30 further comprises an electrical connection 38 that extends from electrode 32 through power source 34, past monitor 36 and through devices 18 and 20. A last portion of circuit 30 extends from devices 18 and 20, through fluid 14 and to electrode 32. Since the conductive material of devices 18 and 20 is covered with an insulative protective material, there will, in preferred embodiments, effectively be no current flow within circuit 30 until the protective material of one or both of devices 18 and 20 is compromised to expose the underlying conductive material to bath 12. Once the protective material is compromised, however, electrons will travel from the exposed underlying conductive material through fluid 14 and to electrode 13, enabling current flow within circuit 30.

Preferably, monitor 36 will be configured to monitor a current flow state of circuit 30. Specifically, monitor 36 will determine if the circuit is in a closed state (which enables a current flow), or in an open state (which does not enable the current flow). If the insulative material of devices 18 and 20 is intact (i.e., the underlying conductive material is not exposed to fluid 14), circuit 30 will be in an open state. On the other hand, if a breach occurs in the insulative material over one or both of devices 18 and 20 to allow underlying conductive material to be exposed to fluid 14, circuit 30 will be in a closed state.

In the shown embodiment, an alarm 40 is coupled with monitor 36. Alarm 40 can be configured to generate one or both of a human-detectable audible signal or a human-detectable visible signal in response to monitor 36 detecting a closed circuit state. Accordingly, alarm 40 can be configured to alert a user that the insulative material on one or both of devices 18 and 20 has been compromised. The user can then replace the devices 18 and 20 before the conductive material of devices 18 and 20 is exposed to a corrosive fluid 14 for a sufficient period of time to cause extensive structural damage to the conductive material of devices 18 and 20 or significantly contaminate the fluid.

Alarm 40 can be considered to be a circuit-state indicator. Such indicator is configured to be different when circuit 30 is closed than when circuit 30 is open. Accordingly, the indicator signals a breach in the insulative material of devices 18 and 20 by changing from a nontriggered state to a triggered state in response to circuit 30 changing from being in the open state to being in the closed state. As indicated above, the difference between a non-triggered state and a triggered state can be a difference in one or both of an audible or visible signal. For instance, the non-triggered state could comprise no audible signal, and the triggered state could comprise a specific audible signal. In other aspects, the non-triggered state could comprise a specific audible signal, and the triggered state could comprise a different audible signal than that of the non-triggered state. In other exemplary configurations, alarm 40 could comprise a signal on a display screen, or could comprise shut-down circuitry configured to remove devices 18 and 20 from fluid 14 upon detection of a change in circuit 30 from open to closed.

Although circuit 30 is described above as changing from open to closed upon a breach in the protective material of devices 18 and 20, it is to be understood that the change does not have to be from a condition of no current flow to a condition of some current flow. Instead, the change could be in an amount of current flow. In other words, the open state can preclude all current flow, or just a predetermined level of current flow. Further, as the amount of current flow could increase with an increasing number, or size, of breaches in devices 18 and 20, monitor 36 could be configured to quantitate an amount of current flow and determine if the current flow exceeds a predetermined value which is greater than zero. Such predetermined value could be chosen to correspond to a value at which significant structural damage to conductive materials of devices 18 and 20 is found to occur. Accordingly, the sensitivity of circuit 30 can be adjusted relative to an amount of damage to the insulative protective material of devices 18 and 20 which will trigger the alarm 40 coupled with monitor 36. Of course, apparatus 10 could be constructed without alarm 40, and instead have values from monitor 36 displayed so that such values could be regularly checked by users of device 10. It is noted that the predetermined value referred to above can be zero in applications in which it is desired to have apparatus 10 with extremely high sensitivity to breaches in the insulative protective material of devices 18 and 20.

Another embodiment of the invention is described with reference to FIG. 2. In referring to FIG. 2, similar numbering will be utilized as was utilized in describing the embodiment of FIG. 1, with differences indicated by different numbers. FIG. 2 shows an apparatus 50 comprising a bath 12, and a pair of semiconductor substrate receiving devices 18 and 20. Apparatus 50 comprises a circuit 60 comprising a power source 34, a monitor 36, and an electrode 32. A difference between circuit 60 of FIG. 2 and circuit 30 of FIG. 1 is that each of devices 18 and 20 is separately connected to monitor 36 in circuit 60, whereas the devices 18 and 20 were connected to monitor 36 through a common connection in circuit 30. The separate (or parallel) connection of devices 18 and 20 to monitor 36 can enable monitor 36 to indicate which of devices 18 and 20 has had a protective coating compromised. Such can enable a person utilizing apparatus 50 to replace only the one of devices 18 and 20 which has had the protective material compromised, rather than replacing both of such devices.

Monitor 36 of apparatus 50 is connected to an alarm 40. Alarm 40 can be configured to generate a different alarm if device 18 has its protective coating compromised than if device 20 has its protective coating compromised. Accordingly, alarm 40 can be configured to identify which of devices 18 and 20 has had a protective coating compromised.

In the discussion above, apparatuses 10 (FIG. 1) and 50 (FIG. 2) are described as comprising two semiconductor substrate receiving devices (18 and 20). It is to be understood that the invention encompasses other embodiments (not shown) where only one semiconductor receiving device is provided, or wherein more than two semiconductor receiving devices are provided.

It is noted that in either of the embodiments described above, if the bath has a low concentration of electrolyte, additional power can be provided to create a current from the conductive material of devices 18 and 20 to electrode 32 when the protective insulative material of devices 18 and 20 is compromised. Accordingly, methodology of the present invention can be utilized with bath solutions which would generally not be considered conductive, such as, for example, deionized water having a conductivity of 18.26 megohm-cm.

Although the invention is described with reference to exemplary embodiments pertaining to semiconductor wafer processing, it is to be understood that the invention is not to be limited to semiconductor wafer processing methods except to the extent that such limitation is recited in the claims which follow. The invention can be utilized for detecting a breach in a protective material in any application in which a conductive material (such as a metal) is coated with an insulative protective material (such as a plastic) and immersed in an electrolytic solution. It can be particularly desirable to detect breaches in the protective material if the electrolytic solution is corrosive for the conductive material.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A semiconductor substrate receiving apparatus configured to establish a current flow state within an electrolytic bath, comprising:
    a conductive substrate support to be submerged in the electrolytic bath, the conductive substrate support coated with electrically insulative material;
    an electrode within the electrolytic bath;
    a power source configured to provide current flow between the electrode and conductive substrate support; and
    a circuit-state indicator comprising an audible signal activated during the current flow between the electrode and conductive substrate support.

2. The apparatus of claim 1 further comprising at least two conductive substrate supports.

3. The apparatus of claim 1 further comprising at least two conductive substrate supports and circuitry being configured to indicate which of the at least two conductive substrate supports has had its electrically insulative material compromised.

4. The apparatus of claim 1 further comprising a monitor configured to monitor the current flow state to determine if an electrical closed state or an electrical open state exists between the electrode and conductive substrate support.

5. The apparatus of claim 4 wherein the electrical closed state indicates the electrically insulative material is not compromised and the electrical open state indicates the electrically insulative material is compromised.

6. The apparatus of claim 4 further comprising an alarm in electrical connection with the monitor and configured to change from a non-triggered state to a triggered state if the current flow state changes from being in the electrical open state to being in the electrical closed state.

7. The apparatus of claim 1 wherein the power source comprises a direct current power source.

8. The apparatus of claim 1 wherein the power source comprises an alternating current power source.

* * * * *

UNITED STATES PATENT AND TRADEMARK OFFICE
CERTIFICATE OF CORRECTION

PATENT NO. : 6,593,759 B2
DATED : July 15, 2003
INVENTOR(S) : Terry Gilton

It is certified that error appears in the above-identified patent and that said Letters Patent is hereby corrected as shown below:

<u>Title page,</u>
Item [56], References Cited, U.S. PATENT DOCUMENTS, insert these following references:

| | | | |
|---|---|---|---|
| -- 4,839,580 | 06/1989 | Moore et al. | 324/65 |
| 4,755,744 | 07/1988 | Moore et al. | 324/65 |
| 4,949,760 | 08/1990 | Wilson et al. | 139/66 |
| 4,495,558 | 01/1985 | Cath et al. | 364/563 |
| 5,081,421 | 01/1992 | Miller et al. | 324/671 |
| 3,924,175 | 12/1975 | Wilson | 324/30 |
| 4,098,651 | 07/1978 | Alder | 204/1 |
| 3,866,117 | 02/1975 | Erdman | 324/54 |
| 5,535,618 | 07/1996 | Konieczka | 73/49.3 |
| 4,791,811 | 12/1988 | Barbee | 73/119 |
| 5,097,214 | 03/1992 | Schinhärl | 324/554 |
| 5,969,532 | 10/1999 | Usui et al. | 324/557 |
| 5,378,991 | 01/1995 | Anderson et al. | 324/557 |
| 4,814,059 | 03/1989 | Nishizawa et al. | 204/406 |
| 5,280,424 | 01/1994 | Rony et al. | 364/148 |
| 5,486,765 | 01/1996 | Izumiya et al. | 324/537 |
| 3,627,662 | 12/1971 | Feuersanger | 204/192 |
| 5,097,214 | 03/1992 | Schinhärl | 324/554 |
| 5,635,410 | 06/1997 | Kusuda | 437/8 |
| 6,114,865 | 09/2000 | Lagowski et al. | 324/755 |
| 3,879,657 | 04/1975 | Nystuen et al. | 324/30 |
| 5,999,006 | 12/1999 | Kikuchi | 324/750 -- |

| | | | |
|---|---|---|---|
| -- 4,686,857 | 08/1987 | Kato | 73/304 |
| 3,969,279 | 07/1976 | Kern | 252/521 |
| 3,636,441 | 01/1972 | Fujimura et al. | 324/64 |
| 4,072,576 | 02/1978 | Arwin et al. | 195/103 |
| 4,473,795 | 09/1987 | Wood | 324/54 -- |

UNITED STATES PATENT AND TRADEMARK OFFICE
CERTIFICATE OF CORRECTION

PATENT NO.    : 6,593,759 B2
DATED         : July 15, 2003
INVENTOR(S)   : Terry Gilton It is certified that error appears in the above-identified patent and that said Letters Patent is hereby corrected as shown below:

<u>Title page cont'd,</u>
FOREIGN PATENT DOCUMENTS, insert these following references:

```
-- EPO    0 277 623 A2    1988
   EPO    0 455 455 A2    1991
   JP     61-67942        1984
   JP     2-71119         1980
   JP     63-165746       1986
   JP     2-237047        1989
   JP     9-213762        1996 --
```

Signed and Sealed this

Twenty-fifth Day of November, 2003

JAMES E. ROGAN
*Director of the United States Patent and Trademark Office*